United States Patent [19]

Blomback et al.

[11] Patent Number: 4,640,778
[45] Date of Patent: Feb. 3, 1987

[54] FIBRIN GEL-CONTAINING FILTER

[75] Inventors: Birger Blomback; Masahisa Okada, both of New York, N.Y.

[73] Assignee: New York Blood Center, Inc., New York, N.Y.

[21] Appl. No.: 395,768

[22] Filed: Jul. 6, 1982

[30] Foreign Application Priority Data

Dec. 30, 1981 [SE] Sweden .................. 8107864

[51] Int. Cl.[4] .................. C12N 7/02; C12N 1/00; B01D 39/00
[52] U.S. Cl. .................. 210/484; 210/500.1; 210/927; 210/500.27; 435/239; 435/317; 436/178
[58] Field of Search .................. 210/500.1, 500.2, 289, 210/489, 484, 490, 927, 635, 658; 435/239, 317, 820, 13; 424/101; 436/177, 178

[56] References Cited

U.S. PATENT DOCUMENTS

| | | | |
|---|---|---|---|
| 3,486,981 | 12/1969 | Speck | 435/13 |
| 3,665,061 | 5/1972 | Eberly, Jr. | 264/49 |
| 3,778,352 | 12/1973 | Bishop et al. | 435/13 |
| 3,972,776 | 8/1976 | Vieth et al. | 195/65 |
| 4,042,733 | 8/1977 | Buchta et al. | 427/391 |
| 4,046,635 | 9/1977 | Moroz | 435/13 |

FOREIGN PATENT DOCUMENTS

| | | |
|---|---|---|
| 2009515 | 2/1970 | Fed. Rep. of Germany . |
| 2025649 | 5/1970 | Fed. Rep. of Germany . |
| 2432049 | 7/1974 | Fed. Rep. of Germany . |
| 2407961 | 8/1974 | Fed. Rep. of Germany . |
| 56-115725 | 9/1981 | Japan . |

OTHER PUBLICATIONS

Chemical Abstracts—vol. 84 & 91—Pharmacodynamics.
Chemical Abstracts—vol. 88—Contribution to the Biochemistry of Anabolic Steroids.
Article, "Fibrin Gel Structure and Clotting Time" by Birger Blomback and Masahisa Okada, Thrombosis Research 25; 51-1970, 1982, Pergamon Press Ltd.
Thrombosis and Haemostasis, No. 1, vol. 46, Jul. 12, 1981, cols. 0757 and 0758, Journal of the International Society on Thrombosis and Haemostasis.
Chemical Abstracts, vol. 95, No. 63, 1981, p. 379, Abstract No. 225655d, "Immobilized Hepatitis-B Virus Antibody in Filters for the Removal of the Virus from Blood."
Chemical Abstracts, vol. 86, No. 13, 1977, p. 343, Abstract No. 69117m, "Microaggregate Formation in Stored Blood IV Influence of Fibrin on Screen Filtration Pressure and Its Removal by Micropore Filters."

*Primary Examiner*—Benoit Castel
*Attorney, Agent, or Firm*—Sprung, Horn, Kramer & Woods

[57] ABSTRACT

There is disclosed a filter comprising fibrin in gel form, the gel having substantially uniform pore sizes, and the filter comprising means for retaining the shape of at least one surface of the gel against deformation when contacted by a flowing medium.

41 Claims, 15 Drawing Figures

Turbidity profile and release of fibrinopeptides during gelation.

—— Optical density
●······● FPA
○······○ FPB

FIBRIN GEL-CONTAINING FILTER

BACKGROUND OF THE INVENTION

1. Field of the Invention

This invention relates to a filter with a definite pore size comprising fibrin and a process for the preparation thereof from fibrinogen. This invention also relates to a size selective process employing the filters of the invention.

2. Discussion of Prior Art

Formation of fibrin gels by contacting fibrinogen with a coagulation enzyme has long been known. It has been observed that when a liquid is passed over the gel, permeation of the gel increasingly becomes difficult—sometimes to the point where permeation and passage of the liquid are rapidly diminished or cease. It was believed that the gel infrastructure was extremely fragile and that the gel consisted of networks of channels and pores of varying size which were highly changeable and highly dependent upon and variable with liquid or liquid mixtures passed thereover, especially one having solid particles.

It was therefore thought that such fibrin gel was not useful in separating components where the separation was effected solely on the basis of particle size.

Specifically, when investigating the fibrin formation from fibrinogen the interest was directed to the flow properties of fibrin gels. It has e.g. been shown before that the flow properties through silica gel as well as through agar and gelatin gels are such as for a viscous flow. It has also been shown earlier that the flow through a fibrin gel is dependent upon the ionic strength and fibrinogen concentration in the preparation. In the investigations made, the permeability coefficient ($K_s$) of the fibrin gels was determined by Poiscuille's law as follows:

$$\text{(Darcy coefficient)} \quad K_s = \frac{Q \cdot L \cdot n}{t \cdot A \cdot \Delta p} \quad (1)$$

wherein Q is the flow through the gel in cm$^3$, A is the gel surface in cm$^2$, $\Delta p$ is the pressure difference in dynes/cm$^2$ (=0.1 N/m$^2$=0.1 Pa), t is the time in seconds, L is the length of the gel in cm and n is the viscosity in poise (=0.1 Pa·s). Moreover, Kozeny-Carman has shown that the following relationship applies in a viscous or laminar flow in a capillary system:

$$m = \sqrt{\frac{K_o \cdot K_s}{\cos^2\phi \cdot \epsilon}} \quad (2)$$

wherein m is the hydraulic radius $$\left(\frac{\text{wettable surface}}{\text{wettable circumference}}\right)$$

in cm, $K_o$ is a factor decided by the geometry of the capillaries, and $\phi$ is the orientation (angle) of the capillaries to the direction of flow, $\epsilon$ is the partial share of liquid in the gel and r is the radius of the capillaries in cm. $\epsilon$ can be calculated by means of the protein concentration and with a knowledge of the partial specific volume of the fibrinogen which is 0.72. For gels of the type concerned here $K_o$ and $\cos\phi$ cannot be calculated.

In the theoretical calculations it has been assumed here that the capillaries are cylindrical and parallel to the direction of flow, which according to Madras et al brings the indicated formula to the following:

$$r = 2m = \sqrt{\frac{8 \cdot K_s}{\epsilon}} \quad (3)$$

The theoretical pore size is therefore 2r. By effective pore size we mean: the size at which particles of smaller size pass through the pores and particles of larger size and retained. It has appeared from the tests that the clotting time (time of gel formation) of the thrombin-fibrinogen mixture, here called Ct, is directly proportional to the flow (Q) through the gel. The flow (Q) has further been found to be inversely proportional to the fibrinogen concentration (C). Provided Q=0, when 1/C=0 and Ct=0, the equation (1) will have the following form:

$$K_s = \frac{k \cdot Ct \cdot K \cdot n}{C \cdot A \cdot P \cdot t} \quad (4)$$

wherein k is a constant which is dependent on pH, ionic strength and calcium concentration and, moreover, is characteristic of the enzyme used in the gel formation, and Ct is the clotting time in seconds. The other symbols are the same as in equation (1). The term t is omitted when the flow is expressed in cm$^3$/s. According to this equation the permeability coefficient $K_s$ is thus directly proportional to the clotting time Ct and inversely proportional to the fibrinogen concentration.

By varying the pH between 6 and 10 the ionic strength between 0.05 and 0.5, the calcium ion concentration between 0 and 20 mM and/or the concentration of enzyme (e.g. thrombin, "Batroxobin" or "Arvin") between 0.01 and 10 NIH-units (or the corresponding units of other enzymes) per ml solution and the fibrinogen concentration from 0.1 and up to 40 g/l, preferably between 1 and 10 g/l, gels with $K_s$-values [calculated according to the equation (1)] between $10^{-7}$ and $10^{-12}$, preferably between $10^{-8}$ and $10^{-11}$, can be prepared. Calculated according to the equation (3), the corresponding average radii will be 0.03–9 $\mu$m, preferably 0.09–2.8 $\mu$m. If FXIII (a transamidation enzyme) and calcium ions are present in the gel formation the stability of the gels will be increased as covalent cross-linkings will arise between the chains in the subunits in the gel matrix.

Thus, now it has been found according to the invention that these fibrin gels can be used as a filter. The filter according to the invention is characterized in that it is built of fibrin and the fibrin gel is in association with a shape-retaining means which retains the shape of at least one surface of said gel against deformation when contacted by a flowing liquid.

The filter of the invention has substantially uniform pores. By that is meant that the standard deviation of pore size is less than 15 percent, preferably less than 10 percent and in some instances less than 5 percent.

The pore size of the gel has, moreover, been found to be a function of the clotting parameters used in the gels' preparation, i.e., the pore size is varied by changing said parameters. The pore size is then proportional to the clotting time.

It has now been discovered, in accordance with the invention, that fibrin in gel form can be used as a filter if means are provided to retain the shape of at least one surface of the gel against deformation when the gel is contacted by a flowing medium such as a flowing liquid medium containing components to be separated. It has also been discovered, quite surprisingly, that the gel has substantially uniform pore sizes and that these pore sizes can be regulated simply by altering the process parameters employed for the formation of the gel.

Specifically, it has been discovered if the gel is in some way stabilized by a shape-retaining means, that the gel structure is preserved and the uniform pores therein function ideally as a filter medium.

Generally speaking, the gel is brought in contact with a shape-retaining means. The shape-retaining means can be a foraminous member such as a foraminous sheet member and is preferably disposed on or in association with an upper surface of the gel, preferably in contact with the gel either directly or through an adhesive or a graft. Since the foraminous member serves to preserve the shape and structure of the upper surface of the gel when the medium to be filtered contacts the same, the gel does not collapse, thereby allowing the uniform pores thereof to function ideally as a filter medium.

Foraminous members functioning as shape-retaining means can have virtually any size and shape, although they are preferably in the form of a sheet and preferably are substantially co-extensive with the upper surface of the gel. The foraminous sheet members can be in the form of a fibrous network such as in the form of a woven or non-woven or knitted fabric, the fibers of which can be natural or synthetic.

When the fibers of a foraminous sheet member are natural, they can be, for example, made of silk, wool, cotton, cellulose, hemp, jute or the like.

As synthetic fibers, there are contemplated in particular fibers made of nylon, polyester, polyolefin, fibers made of vinyl polymers, acrylics such as polyacrylonitrile, rayon, to name a few.

The fibers generally have a thickness between 1 $\mu$m and 1000 $\mu$m, preferably between 10 and 20 $\mu$m, and are disposed in relationship to one another to define openings therebetween of between 0.01 and 5 mm, preferably between 0.05 and 1 mm, it being understood that the size of the openings between the fibers of the foraminous sheet is not especially critical, provided it allows passage therethrough of the medium to be filtered. It is preferred that as much fiber be in contact with or adhere to the gel as possible so as to insure maximum structural integrity of the surface of the gel initially to come in contact with the medium to be filtered.

Instead of using a fibrous foraminous member, one can use one made of wires, such as wires made of copper, tin, zinc, aluminum, glass, boron, titanium, steel, stainless steel, etc. The wires function analogously to the function performed by the fibers in providing structural integrity to at least one surface of the gel, preferably the upper surface or surface which is to be initially brought in contact with a mixture to be filtered. The interstices between the wires are of the same magnitude as the interstices between the fibers of a woven, non-woven or knitted fabric serving as a foraminous sheet member. The wires can be in the form of a screen, wire mesh or an expanded wire sheet and are preferably co-extensive with at least one side of the gel, preferably the upper surface.

The gel has uniform pores but owing to the manner by which the gel can be formed, can have uniform pores over a wide range. Preferably, the substantially uniform pores of the fibrin gel have a theoretical pore size or diameter in the range of about 0.003 to 1 $\mu$m, more preferably 0.009 to 0.3 $\mu$m.

The gel is formed by contacting fibrinogen with an enzyme, especially a coagulation enzyme. Particularly contemplated enzymes for use in forming a fibrin gel include thrombin, Batroxobin, Arvin, Eccarin, Staphylocoagulase, Papain, Trypsin, caterpillar venom enzyme, etc.

Generally speaking, the gel formation is effected at room temperature, although temperatures from $-3°$ C. up to 58° C. can be employed. Preferably, the temperature is in the range of 0° to 40° C.

It is preferred that the gel be formed by contacting the fibrinogen with an enzyme in the present of calcium ions. The calcium ion concentration can be up to 20 mM. The presence of calcium ions is not required in all instances. Where thrombin is employed as the coagulation enzyme, the gel can be formed in the absence of a calcium ion.

In forming the gel, there is generally employed 0.1 to $10^{-5}$ enzyme units per gram fibrinogen, preferably 10 to $10^{-3}$ enzyme units per unit weight fibrinogen. Following formation of the gel whose coagulation time is a function of the relative amount of enzyme to fibrinogen as well as the concentration of calcium ion, the gel is preferably hardened or set by crosslinking the components thereof by contacting the gel with a crosslinking agent. Crosslinking agents contemplated include bis-imidates such as suberimidate, azides like tartryl di($\epsilon$-amino carproylazide), aryl dihalides like 4,4-difluoro-3,3'-dinitrophenyl sulfone, glutardialdehyde, nitrenes, N,N'(4-azido-2-nitrophenyl)-cystamine dioxide, cupric di(1,10-phenanthroline), dithio bis-(succinimidyl propionate), N,N'-phenylene dimaleimide as well as polyethyleneimides and other bifunctional compounds, especially those known to crosslink with epsilon lysine, alpha amino groups, carboxy groups of aspartic and glutamic acids, and hydroxyl groups of amino acids in the protein chain (e.g. threonine and serine).

Bis-imidates which can be used include those of the formula

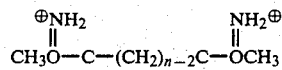

wherein n=3 to 15 especially 3 to 10.

Azides which can be used include substituted and unsubstituted azides of the formula

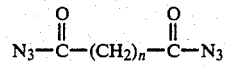

wherein n=1 to 20 especially 1 to 15. Azides contemplated include those having a hetero atom in the chain, especially nitrogen. Also contemplated are hydroxy substituted azides.

Aryl dihalides which can be used include those having mono, poly and fused rings as well as rings joined by a direct bond or through a methylene bridge or a sulfo bridge. The halogen of the halide can be fluorine, chlorine, or bromine. The compounds can be substituted by inert or functional groups such as nitro, or disulfide. Contemplated compounds include those where a functional group has replaced one of the halo substituents, e.g. nitro. Compounds contemplated include

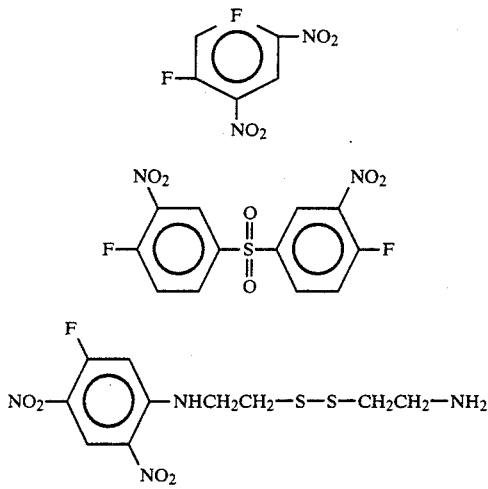

Especially contemplated is glutardialdehyde.

Generally speaking, the crosslinking agent is employed in an amount of between 0.001% and 8% by weight, preferably between 1 and 2% by weight of the gel for 1-120 minutes. Crosslinking is effected at temperatures of between 10° and 40° C., preferably 20° to 25° C. After the hardened or crosslinked structure is obtained, the gel is usually washed free of extraneous material.

The gel in such hardened form is useful as a filter, i.e., without any foraminous sheet material. Preferably, however, the gel is formed on or in association with a shape-retaining means such as a net, wire mesh or other sheet material and while in contact with such shape-retaining means is hardened by the use of a hardening or crosslinking agent.

Preferably, the gel is supported on its upper and lower surfaces by a shape-retaining means such as a foraminous sheet or the like, whereby to insure that the gel retains its shape during use as a filter.

This invention further contemplates a process for separating a first substance having a theoretical size of 0.003 to 1 $\mu$m from a second substance having a larger size which comprises passing a mixture of said first and second substances over a filter comprising fibrin in gel form and having pores of substantially uniform size, said filter having means for retaining the shape of at least one surface of said gel against deformation when contacted by a flowing medium, wherein the effective pore size of said fibrin gel is larger than the particle size of said first substance and smaller than the particle size of said second substance. Preferably, the pores of the gel have a theoretical size of 0.009 to 0.3 mm.

The filters of the invention are important, as they permit the separation of bacteria and viruses from mixtures containing the same. The ability to regulate the pore size and to achieve a gel of uniform pore size is an important and critical characteristic of the filters of the invention. These filters permit the separation of blood components, the separation of components of blood plasma, the removal of platelets from blood, the fractionation of cells and cell fragments and the separation of high molecular weight protein aggregates. In addition, a variety of particles such as latex, silica, carbon and metallic particles may be separated over these filters. Components which can be separated include those shown in the table below:

TABLE A

| Material A Separated | Material from Which Material "A" is Separated | How Separated | | Effective Pore Size Range for Filter |
|---|---|---|---|---|
| | | Retained | Eluted | |
| Blood platelets | Blood plasma | X | | Below 1 $\mu$m |
| Red blood cells | " | X | | 1 $\mu$m and below |
| Sendai virus | Culture medium | X | | 0.1 $\mu$m and below |
| " | " | | X | 0.2 $\mu$m and above |
| Liver mitochondria | Cyto plasma | X | | 0.5 $\mu$m and below |
| " | " | | X | 0.5 $\mu$m and above |
| Adeno virus | Culture medium | X | | 0.05 $\mu$m and below |
| " | " | | X | 0.1 $\mu$m and above |
| E. coli bacteria | " | X | | 1 $\mu$m and below |
| FVIII complex | High molecular weight material (h. m. w) separated from low molecular weight material (l. m. w) | X (h. m. w) | X (l. m. w) | 0.05 $\mu$m and below |
| Blood leucocytes | Blood plasma | X | | 1 $\mu$m and below |
| Blood lymphocytes | " | X | | 1 $\mu$m and below |

Fibrin gel filters have above all the advantages over other gel filters that the pore size can be simply varied as desired. Moreover, the present filters have high flow rates at such pore sizes as can be used to remove very small particles, such as virus particles. In this respect, the filters of the invention are more suitable than known membrane filters and filters of polyacrylamide gels. The absence of absorption of protein on the filters is also an advantage as compared with certain other filters.

DESCRIPTION OF SPECIFIC EMBODIMENTS

The process according to the invention for the preparation of gel filters is as described above, characterized in that a fibrinogen solution with preadjusting clotting parameters is mixed with a coagulation enzyme and the resulting mixture is made to clot in a form intended for the filter. It may be convenient to strengthen the fibrin gel formed during or after clotting by a shape-retaining means of greater strength than the gel which is preferably applied to the upper surface of the gel to be prepared and preferably to both the upper and lower surfaces thereof.

The shape-retaining means (reinforcing meshes) are preferably in the form of a net which is applied at the lower and preferably also at the upper surface in the mold in which the fibrinogen mixture is poured (cast). This mixture can preferably penetrate the net (foraminous sheet material) e.g. have its surface 10 μm–5 mm, preferably 0.5–2 mm, from the net. The net can have a mesh width, for example, 10 μm to 5 mm, preferably 50 μm–1 mm and the wire diameter can be, for example, 0.01–1.0 mm, preferably 0.1–0.5 mm, where wires are employed as shape-retaining means. In addition to the metallic wires noted above, wires of natural fibers and plastics can also be employed. The filter can also be reinforced in other places than at the surfaces. It can, for example, be built on a foam material, such as a plastic foam, which can support part of the entire filter.

The filters of the invention, especially in a non-hardened or crosslinked form, should not be subjected to temperatures in excess of 100° C., as such heat sterilization tends to destroy the gel structure. It is, therefore, necessary in utilizing the filters for biological processes to prepare them sterilely from the beginning. On the other hand, it has been found possible to harden or crosslink the filter during the preparation by carrying out the gel formation in the presence of Factor FXIII and calcium ions. Where Factor FXIII is to be present, it is preferably present in an amount of at least 5 units per gram fibrinogen, preferably at least 50 units per gram. Calcium is present in a concentration of at least 20 mM.

A still stronger filter is obtained by effecting crosslinking with one of the above-mentioned crosslinking agents, especially a dialdehyde and particularly one of the formula OCH—R—CHO, wherein R is an alkylene group of 1 to 8 carbon atoms, such as glutardialdehyde. The filter obtained in this way can be heat treated in an autoclave and consequently sterilized.

The clotting parameters are above all the enzyme concentration, e.g. between 100 and 300 NIH units/L for thrombin and for the fibrinogen concentration between 0.1 and 70 g/l, preferably between 1 and 10 g/l, increased concentration giving a tighter gel. A tighter gel has a smaller pore size. Increased ionic strength also provides a tighter gel as well as a higher pH. It is preferred to carry out the gel preparation using a gel mixture having a pH of between 5.5 and 11, preferably between 6 and 9, and an ionic strength between 0.05 and 0.5. Gels formed at calcium ion concentrations between 0 and 20 mM are tighter.

Pore size is also affected by the temperature at which the clotting (gelation) is effected. A lower temperature of gelation means an increased clotting time, which in turn means that the resultant gel has a larger pore size. As a result of its larger pore size, it provides a greater rate of flow.

The gel of the invention can be used other than as a filter. One can dispose catalytically active substances such as catalytically active enzymes or catalytically active metals within the pores and thus use the pores' structure as a catalyst. The filter, therefore, can act more or less as a catalyst support for the catalytically active agent disposed therein. When the catalytically active agent is disposed within the pores, the resultant structure can be employed as a size selective catalyst converting only those components whose size is such as to freely pass through the pores of the catalyst support. Those materials retained in the surface of the gel are not catalytically converted.

By such a filter, one can conveniently effect enzymatic conversions, especially when the enzyme is immobilized within the filter covalently, ionically or otherwise. Since the gel structure is formed by the use of an enzyme, the filter of the invention's chemical components is compatible with the enzyme being employed as an enzyme catalyst. Thus, one can use the filter of the invention for any of the following enzyme conversions when the same contains the appropriate enzyme to effect that enzymatic catalysis: for reactions involving various oxido-reductases, transferases, hydrolases, lyases, isomerases and ligasis (synthetases). Hydrolases which have capacity of degrading the protein strands in the gels cannot be used.

The method by which the enzyme or other catalytic component is disposed within the filter, i.e., within the pores of the filter, depends upon the nature of the enzyme. Preferably it is disposed by the use of a known enzyme immobilizing agent followed by washing of the filter to remove extraneous materials.

One can also dispose reactive cellular components within the pores of the gels. Upon reaction, low molecular weight components may be released and subsequently eluted from the gels. An example of such a type of reaction is production of interferon by leukocytes after their reaction with Sendai virus. As shown in this invention, both of these components can be disposed within the pores of the gels.

BRIEF DESCRIPTION OF DRAWINGS

The invention is described more in detail with reference to the enclosed drawing, in which.

Figure 1A:
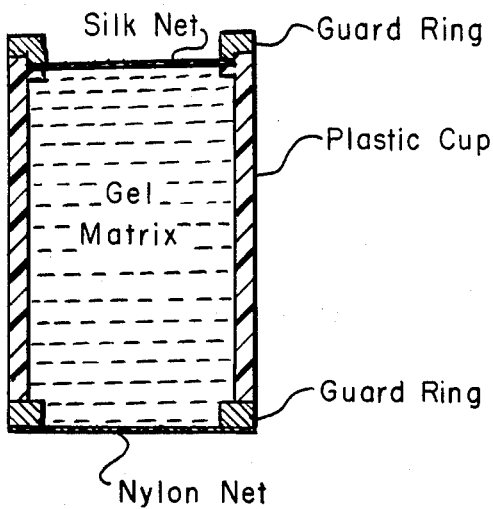
FIG. 1a shows molding of a filter according to the invention.

In order to more fully illustrate the invention and the manner of practicing the same, the following examples are presented.

EXAMPLE 1

METHODS AND MATERIALS

Human fibrinogen, Fraction 1-4 (7) was obtained from IMCO, Stockholm, Sweden. The preparation, either a freeze-dried powder or a wet paste, was 97-100% clottable (as determined spectrophotometrically). A solution being 0.3M in NaCl and 2% in protein was prepared. This solution (50 ml) was dialyzed against 0.3M NaCl at 4° for 3 hrs. with changes of outer fluid (5 liter) every hour. This dialyzed solution was further diluted with deareated Tris-imidazole buffer (8) of pH between 6.5 and 8.2 to protein concentrations between 1.2 and 5.0 g/l. In the final dilutions the concentration of each Tris and imidazole was 0.02M. When necessary increase in ionic strength was achieved by inclusion of sodium chloride in the buffer. In order to inhibit any trace of plasmin which may be generated, Trasylol (Bayer AG, Germany) was added to a concentration of 5 KIE/ml to all buffers and dialysis fluids.

In the gelation experiments the following procedures was employed: To 3.65 ml of fibrinogen solution in a plastic tube was added 70 μl of 1M $CaCl_2$ solution, immediately followed by 50 μl of thrombin or Batroxobin solutions of varying concentrations. This mixture is called Reaction Mixture. The tubes are rapidly inverted twice and transferred to the gel cup or to the spectrophotometer cell within 10 seconds after addition of enzyme. The further handling is described under separate paragraphs.

Thrombin. In most experiments a bovine preparation prepared as previously described (9) was used. Specific activity: 100-200 NIH units per mg. Control experiments with highly purified (specific activity: about 2000 NIH units per mg human thrombin (10) was performed in some instances.

Batroxobin (from *Bothrops marajoensis*) was obtained from Pentapharm AG, Basel, Switzerland. Specific activity: 505 BU per mg.

Hirudin was also obtained from Pentapharm AG. Specific activity: 1000 ATU per mg.

Reagents. All reagents used were of analytical grade.

PREPARATION OF GEL COLUMN

A solution of thrombin is added to a solution of fibrinogen in a tris-imidazole buffer containing calcium salts with a pH of between 6.5 and 8.2 and an ionic strength between 0.1 and 0.3 so that the final concentration is between 0.05 and 2.5 NIH-units per ml. In other tests Batroxobin is used to obtain gel formation in a concentration between 0.27 and 3.6 BU per ml. The concentration of "Tris" and imidazole salts is each 0.02M and the concentration of calcium salt is also 0.02M. The variation in ionic strength is obtained by addition of NaCl.

Gels are also prepared at calcium ion concentration between 0 and 20 mM. With reduced calcium ion concentration the opacity of the gels is increased. When thrombin is used to achieve the gel formation the clotting time (Ct), also in the absence of calcium ions is directly proportional to the flow rate and thus also to $K_s$. When "Batroxobin" is used for the gel formation, the stability of the gels in the absence of calcium ions is unsatisfactory, which makes flow measurements more difficult.

After addition of an enzyme such as thrombin or Batroxobin, the solution is rapidly mixed and then poured into a cup, e.g., such a one shown in FIG. 1a. It is made of acrylic plastic (other materials can also be used such as nylon and polystyrene) and has an inside diameter of about 14 mm and a height of about 27 mm. The plastic cup is shown in FIG. 1a and the lower part of the cup is provided with a nylon filter having a mesh size of 80×80 μm. This filter is fastened by a plastic guard ring. A film layer, e.g., "Parafilm ®", is preferably applied at the lower portion so that liquid is prevented from leaking out of the cup. Immediately after introducing the solution into the cup, a silk net with the mesh size 150×180 μm is adapted at the upper end and is fastened with a guard ring. The liquid in the gel cup can e.g., be about 1 mm over the net surface. The cup is left at room temperature for at least 2 hours for complete gel formation, preferably in a place free of vibrations.

Figure 1B:
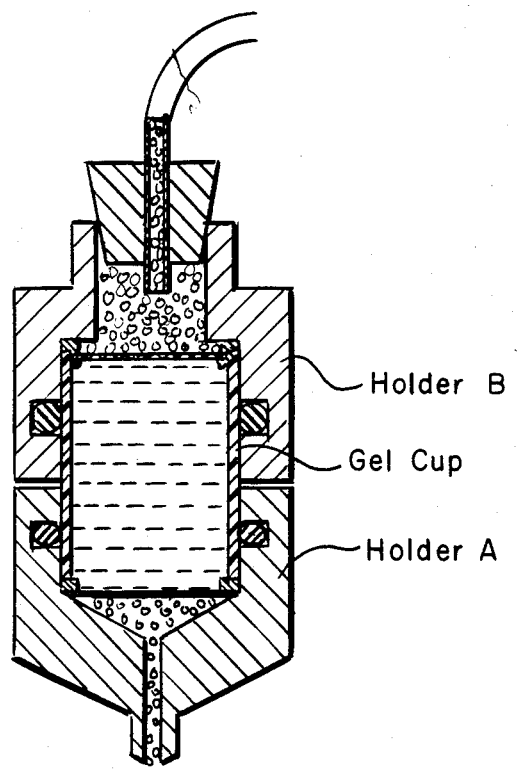
FIG. 1b shows the filter arranged for filtering.

After this time, the film is removed at the lower portion of the cup with its contents of gel is placed in the holder A according to FIG. 1b, a holder B is applied over the upper end of the cup 1. At the upper end of the holder B there is an opening as well as at the lower end of the holder A. The holder B is filled with liquid (buffer or water) and a rubber cork provided with a tube, which is connected with a rubber hose is inserted into the opening. The rubber hose is connected with a container for permeation solution which is allowed to fill the rubber hose without air bubbles. The container (not shown in the drawing) is placed at such a height that a suitable flow is obtained through the gel. The hydrostatic pressure is varied at different tests between 4 and $40\times10^3$ dynes/cm$^2$.

The fibrinogen used for the preparation of the gels contains trace amounts of factor XIII, which is a transamidase. In the presence of this enzyme and calcium ions, covalent intermolecular cross linkages between chains in the molecule units of the fibrin gel are formed. This is especially the case when thrombin is present as thrombin activates factor XIII.

An electrophoretic analysis of reduced fibrin from various gels in the presence of sodium-dodecyl sulphate shows that a complete cross-linking of the α and γ-chains of the fibrin takes place in the presence of thrombin. A partial cross-linking takes place in the presence of Batroxobin. The covalent cross-linkings formed in the presence of factor XIII contributes to the stabilization of the gel structure.

The silk net applied to the top of the gel cup and which is in intimate contact with the gel matrix is of great importance for the mechanical stability of the gels. Without this net or some other means for preventing collapse of the gel, the gel compound is destroyed in the flow tests, the gel collapsing in the central protion and a conical inward bend arising.

The silk net can, of course, be replaced with other nets, e.g., of cotton, nylon, iron or copper, which also stabilize the gel structure at pressures up to $40\times10^3$ dynes/cm$^2$.

Turbidity measurements

Figures 8A, 8B, 8C:
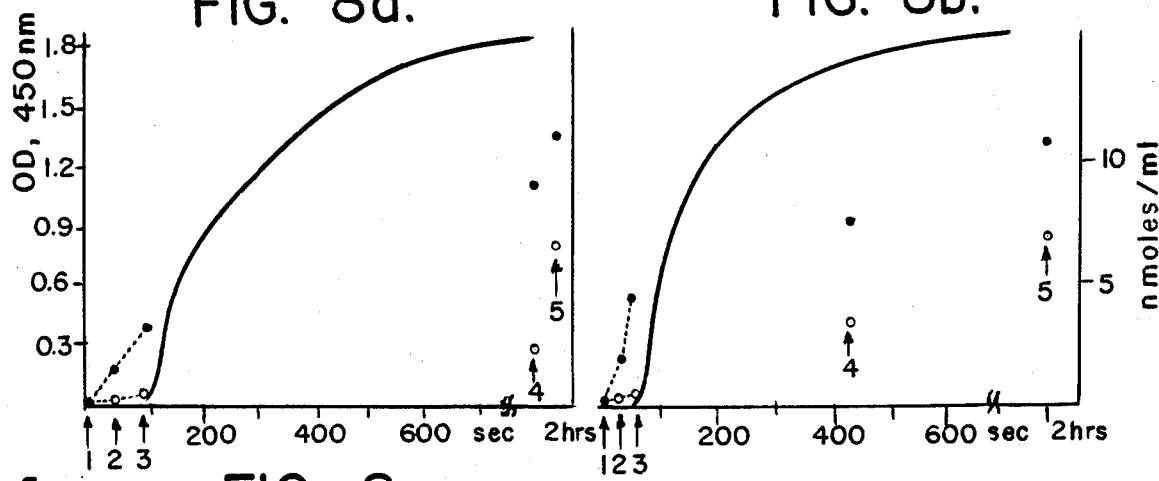
FIGS. 8a, 8b and 8c are graphs plotting activation of fibrinogen and clotting time (Ct).

In parallel to the flow studies, the turbidity profile of the system was determined under identical conditions. In these experiments the Reaction Mixture (see under Fibrinogen) was poured into a cuvette (5 ml) of a recording spectrophotometer (Beckman Acta III) and the turbidity (optical density) recorded at 450 nm. After a lag-phase there was a rapid increase in turbidity (cf. FIG. 8) which was accompanied by gelation. A tangent was drawn to the steepest part of the sigmoidal curve. Its intersection with the time axis is defined as the gelation or clotting time (Ct). (Ct is about the same as the time for visually observed turbidity increase in the gel cup.) In addition to Ct also maximum turbidity (ODmax) and rate of turbidity increase ($\Delta$OD/min) was recorded. The time required for gelation to reach completion was judged from the turbidity curve. This time ranged from 1 hr. to 2 hrs. for the high and the low enzyme concentrations, respectively.

Determination of fibrinopeptides and cross-linking

Reaction Mixtures (see under Fibrinogen) were prepared in several indentical tubes. One of them was used for turbidity measurement as described above. The other tubes contained each 1 ml of Reaction Mixture. The reaction in the latter tubes was quenched at different times by addition of hirudin (2 ATU/ml) and an equal volume of 8M urea. Thereafter the fibrin (ogen) was precipitated by addition of an equal volume of chilled ethanol. The mixtures were kept on ice-bath for 2 hrs. and thereafter the precipitates were secured by centrifugation, dissolved in urea and used for SDS-gel electrophoresis. The supernatants were used for radio-immunoassay (RIA) of FPA, FPB and B$\beta$ 15-42 was assayed using the recently developed method of Kudryk et al.

Viscosity was determined with a viscometer type Ubbelohde, having a flow time for water of about 290 sec at 25° C. It was calibrated against a standard (CNI. Cannon Instrument Company, Pa. USA). Density was determined with a 5 ml pyknometer.

Pore size. The equation for calculation of average pore size of membrances (18) and acrylamide polymer gels (4) was applied:

$$r = \sqrt{\frac{8Ks}{\epsilon}} \quad (2)$$

where r is the average pore radius (in cm), and $\epsilon$ is the fractional void volume of the gel, i.e., the fractional volume of liquid in the gel. $\epsilon$ is calculated on the basis of protein concentration assuming a partial specific volume for fibrinogen of 0.72 (19), $\epsilon$ is in this case the fractional void volume for gels in which no water is bound to the gel matrix. However, the degree of hydration of fibrinogen in solution has been reported as high as 6 g per g protein (20). Assuming that this water is retained by the gel matrix we also calculated $\epsilon$ for such hydrated gels.

Diffusion coefficient. The apparent diffusion coefficient of water in the gel was calculated from Ks according to Ticknor (21) and White (4).

$$D = \frac{R \cdot T \cdot Ks}{\epsilon \cdot V \cdot \eta} \quad (3)$$

where D is the diffusion coefficient (in cm$^2$/sec.). R is the gas constant (in ergs/mole-degree), T it the absolute temperature (in °K) and V is the molar volume of the permeant (in cm$^3$/mole).

Ionic strengths were calculated on basis of the molarity of the electrolytes. Activity coefficients and degree of calcium binding to protein were not taken into account.

Least square analysis was used for calculation of correlation coefficients, slopes and intercepts. All lines shown in figures were drawn accordingly.

RESULTS

Preparation and stability of gels

The flow studies were performed on gels which had been formed at ambient temperature. The average temperature was 24±2°. However, in each series of experiments the variation in temperature never exceeded 2°. Preliminary experiments suggested that this variation in temperature has a negligable effect on the Ct of the system. In the permeation experiments, when not otherwise stated, the flow-rates were corrected to 25°.

The silk net at the upper end of the gels stabilizes the gel structures. Without support of the silk net, the gels will yield to flow at the pressure applied (about 7×10$^3$ dynes/cm$^2$). The yielding is only noted at the center of the gel, since the gel matrix adheres firmly to the walls of the plastic cup.

The nets in the column do not significantly reduce the flow-rate of liquid in columns without gels. We, therefore, assume that also when the nets are in contact with gels they do not restrict the area available for flow.

Before a flow experiment was started, the extent of incorporation of fibrinogen into the gel matrix was determined. This was done by determining the protein content in the void volume of the column (about 4 ml). The amount of protein, as measured spectrophotometrically using the extinction coefficient of fibrinogen (22), ranged between 1 and 3% of the total protein used for gelation. When deemed necessary the non-clottable portion was taken into account in calculations of the fibrin content of gels.

The effect of changing permeant on the flow-rate of gels was studied in some experiments. A representative series of experiments is shown in Table I. The gel was first percolated with buffer of ionic strength 0.21 (experiment I). On changing the permeant to water (experiment II) an increase in flow-rate occurred, which is larger than expected on the basis of the viscosity change of the permeant. On return to the original permeant (experiment III) the flow-rate decreased, but not completely to the original value (experiment I). When buffer of ionic strength 0.36 was percolated through the gel (experiment IV) a small decrease occurred which was almost as expected on the basis of the difference in viscosity between the two buffers. When the permeant was again changed to water (experiment V) the flow-rate increases to almost the same value as after the first change to water (experiment II). These results suggest that the final gel structure is not influenced by moderate changes in permeant composition, but changes may occur on drastic changes in ionic environment and these are not completely reversible.

TABLE I

Flow Properties of Fibrin Gels with Different Permeants. Gel formation: Tris-imidazole buffer pH 7.4, ionic strength 0.21, thrombin 0.8 NIH-units/ml, temperature 21° and fibrinogen concentration 2 mg/ml. Permeation: at 22°–23.5°.

| Experiment | Permeant | Flow, ml/hr | % |
|---|---|---|---|
| I | Tris-imidazole pH 7.4, Γ/2 0.21 | 3.177 | 100 |
| II | H$_2$O | 3.708 | 117 |
| III | Tris-imidazole | 3.385 | 106 |

TABLE I-continued

Flow Properties of Fibrin Gels with Different Permeants.
Gel formation: Tris-imidazole buffer pH 7.4, ionic strength
0.21, thrombin 0.8 NIH-units/ml, temperature 21° and fibrinogen
concentration 2 mg/ml.
Permeation: at 22°–23.5°.

| Experiment | Permeant | Flow, ml/hr | % |
|---|---|---|---|
| IV | pH 7.4, Γ/2 0.21 Tris-imidazole | 3.271 | 103 |
| V | pH 7.4 Γ/2 0.36 H$_2$O | 3.649 | 115 |

Flow pattern through fibrin gels

Viscous flow. In order to test if the flow obeyed Poiseuille's law, the flow-rate at different pressures (4.5–5.6×10$^3$ dyne/cm$^2$) for gels formed at pH 7.4, ionic strength 0.21 was determined, at three different thrombin concentrations (0.1–0.8 NIH units/ml). The Ks-range for these gels was 10$^{-8}$ to 10$^{-10}$. Permeation was in one experiment with the same buffer as above and in the other cases with water. In all cases the drop-rate decreased linearly with decreasing pressure. As shown in Table II for one of the gels, the flow-rate per unit pressure was almost independent of total pressure.

In another series of experiments the flow-rates were determined with permeants of different viscosities. The gels used in these experiments were formed at pH 7.4, ionic strength 0.21, at four fibrinogen concentrations. Thrombin as well as Batroxobin were used as inducers of gel formation. Permeation was performed at five different temperatures between 4.5° and 40°. In all cases there was a linear relationship between the inverse viscosity of the permeant and the flow-rate. These experiments suggest that the flow through the gels is viscous. In addition Reynold's number was calculated and found to be within the laminar region for all gels.

Diffusive flow. It was pointed out by Ticknor, J. Phys. Chem 62, 1483-5 (1958) that the equation for viscous flow is identical in form to equations for diffusive flow, when the relationship between diffusion coefficient (D) and viscosity according to Johnson and Babb, Chem. Revs. 56, 387–453 (1956) is taken into consideration. The relation between Ks and D is given in Equation 3. In flow experiments using water as permeant we calculated the apparent diffusion coefficient for water at 22°–23°. Even for the tightest gels (Ks 10$^{-10}$), the calculated D-values were 6-orders of magnitude larger than the reported self-diffusion coefficient of water at 25° (2.8×10$^{-5}$ cm$^2$/sec.). This supports the above conclusion that the flow through the fibrin gels is predominately viscous.

TABLE II

Relationship Between Pressure and Flow-Rate.
Gelformation: pH 7.4, ionic strength 21, thrombin 0.1 NIH unit/ml,
temperature 23.5° and fibrinogen concentration 2 mg/ml.
Permeation: H$_2$O, temperature 23.5°. Ks = 9 × 10$^{-9}$

| Pressure, dyne/cm$^2$ | % | Flow ml/hr | Flow per dyne per cm$^2$ ml/hr × 10$^3$ | % |
|---|---|---|---|---|
| 5531 | 100 | 11.280 | 2.0394 | 100 |
| 5319 | 96.2 | 10.817 | 2.0337 | 99.7 |
| 5127 | 92.7 | 10.418 | 2.0320 | 99.6 |
| 4874 | 88.1 | 9.859 | 2.0228 | 99.2 |
| 4576 | 82.1 | 9.148 | 1.9991 | 98.0 |

Gel Permeability and clotting time (Ct)

There is a correlation between clotting time (Ct) of fibrinogen and enzyme concentration. We explored the relationship between Ct and permeability of the final gels. Therefore, at the same time as gels were prepared for permeability studies, the Ct of the gel forming system was determined in parallel experiments by turbidity measurements (see Methods).

PH. At a constant fibrinogen concentration and ionic strength, the flow-rates for both thrombin and Batroxobin gels were directly related to the Ct of the gel forming system over a wide range of Ct (17 sec–500 sec). This applied to three different pH's (6.5, 7.4 and 8.2) as exemplified in FIG. 2. At all pH's there was a difference in slope between curves for thrombin as compared to those for Batroxobin.

At each pH, the correlation coefficients (r) for six different Ct versus flow-rate curves (4 experimental points in each) were calculated. The mean r-values and their standard deviations (SD) were as follows: at pH 6.5, 0.9709±0.0184; at pH 7.4, 0.9721±0.0394; at pH 8.2, 0.9599±0.0434. There was no significant difference in r-values for thrombin and Batroxobin curves.

Ionic strength.

In another series of experiments the ionic strength of the gel forming system was, at constant protein concentration, varied between 0.21 and 0.31. At all pH's (6.5, 7.4, 8.2) an increase in ionic strength from 0.02 to 0.3 resulted in a decrease in flow-rate by roughly one order of magnitude. This applied to both thrombin and Batroxobin gels.

Figure 4B:
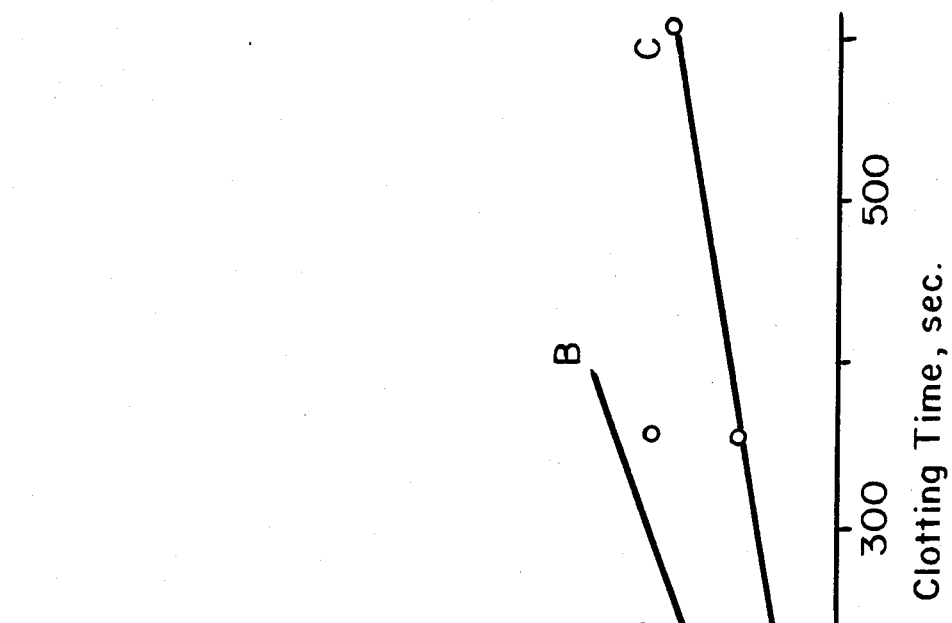
FIGS. 4a and 4b show the flow as a function of the coagulation time at different ionic strength of thrombin and Batroxobin, respectively.
Figure 4A:
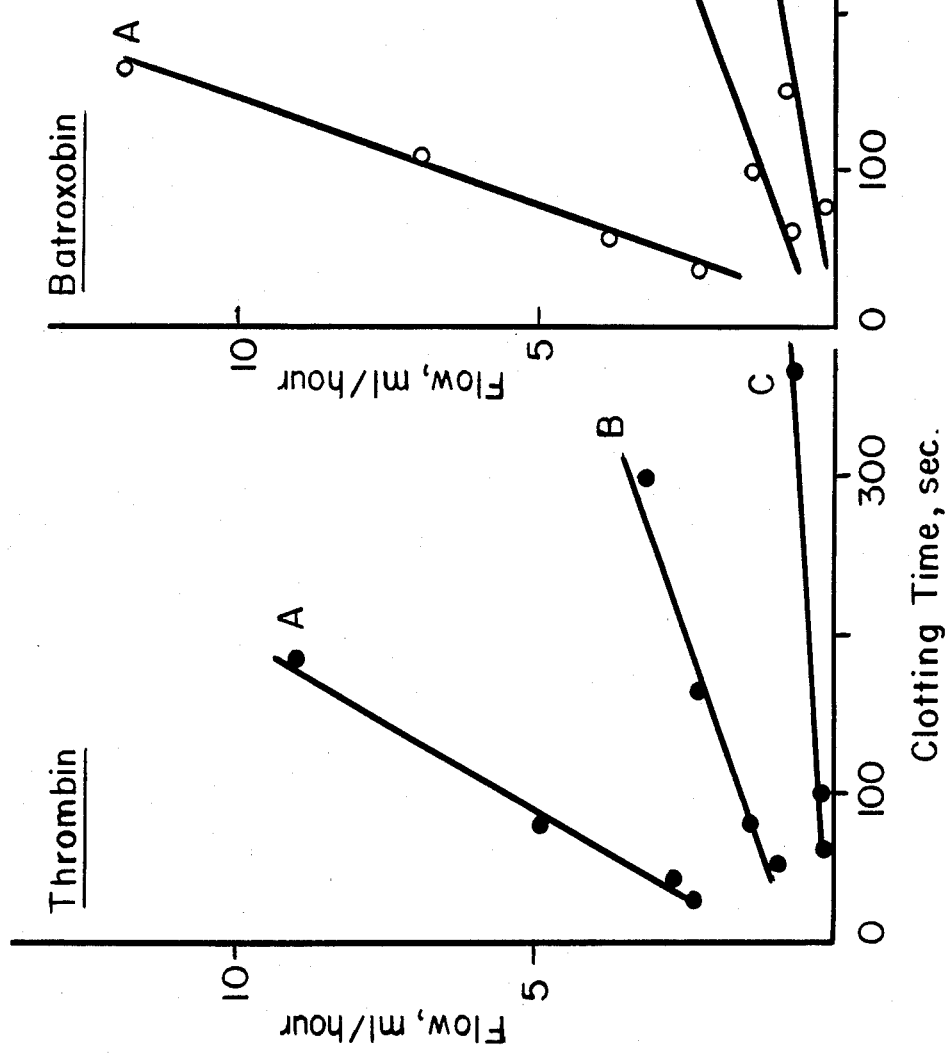

Ct were prolonged with increasing ionic strength at all enzyme concentrations and pH's. At each ionic strenth, however, there was for both thrombin and Batroxobin gels a linear relationship between Ct and flow-rate. The results at pH 7.4 is shown in FIG. 4. At all ionic strengths a difference in slope between curves for thrombin as compared to those for Batroxobin was noted.

At two ionic strengths, regardless of pH, r-values for six different Ct versus flow-rate curves (4 experimental points in each) were calculated. Mean r-values and SD were as follows: at ionic strength 0.21, 0.9851±0.0208 and at ionic strength 0.26, 0.9511±0.0470. There was no significant difference in r-values for thrombin and Batroxobin curves.

Gel permeability and fibrinogen concentration

In a series of experiments we showed that the relationship between Ct and flow-rate applied to a wide range of protein concentrations in the gel forming system. These experiments were only performed at pH 7.4 and ionic strength 0.21. When Ct at a given protein concentration were plotted against flow-rates a linear relationship, similar to that shown in FIG. 3 (pH 7.4), was demonstrated at all fibrinogen concentrations (1.5–5.0 g/l). The plots for both thrombin and Batroxobin converged towards an intercept near the origin with decreasing clossing times. Like in the experiments shown in FIG. 2, the slopes for Batroxobin curves were steeper than those for thrombin at all protein concentrations. The r-values for 8 different Ct versus flow-rate curves (8 points in each) were calculated. Mean r-values and SD were as follows: for thrombin, 0.9800±0.0157 and for Batroxobin, 0.9830±0.0187.

Table III shows Ct at different protein and enzyme concnetrations in one series of experiments. In case of Batroxobin, increasing protein concentrations did not markedly influence Ct. However, in the case of thrombin there is a small prolongation ;of Ct with increasing fibrinogen concentrations.

Figure 5B:
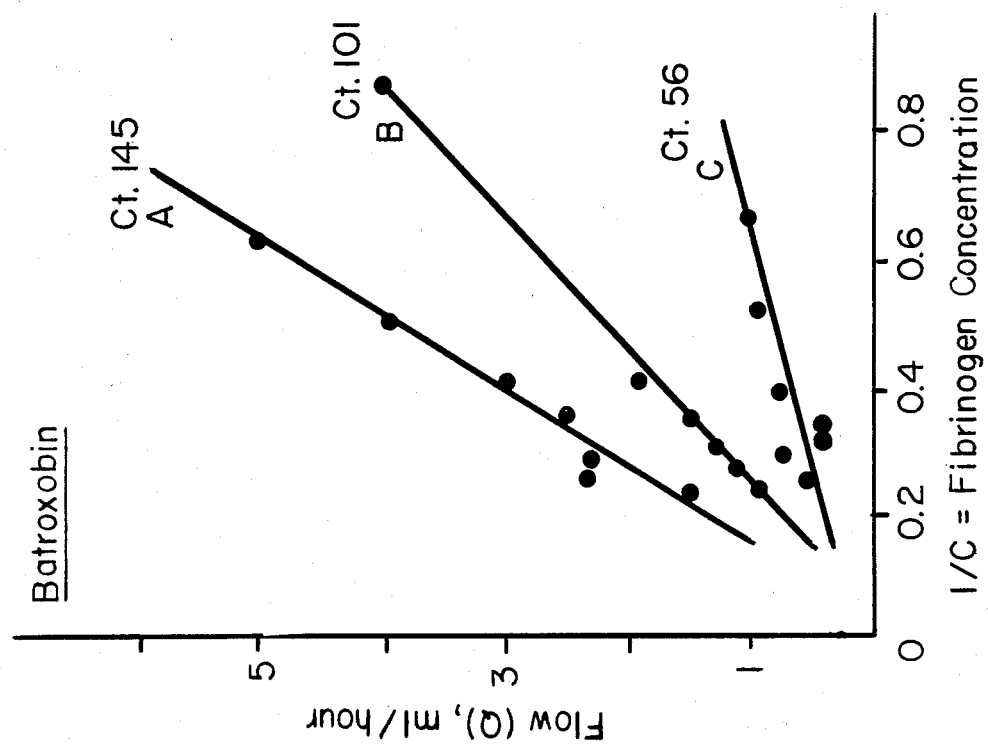
FIGS. 5a and 5b are graphs showing the relationship between protein concentration in the gel forming system and flow-rate.
Figure 5A:
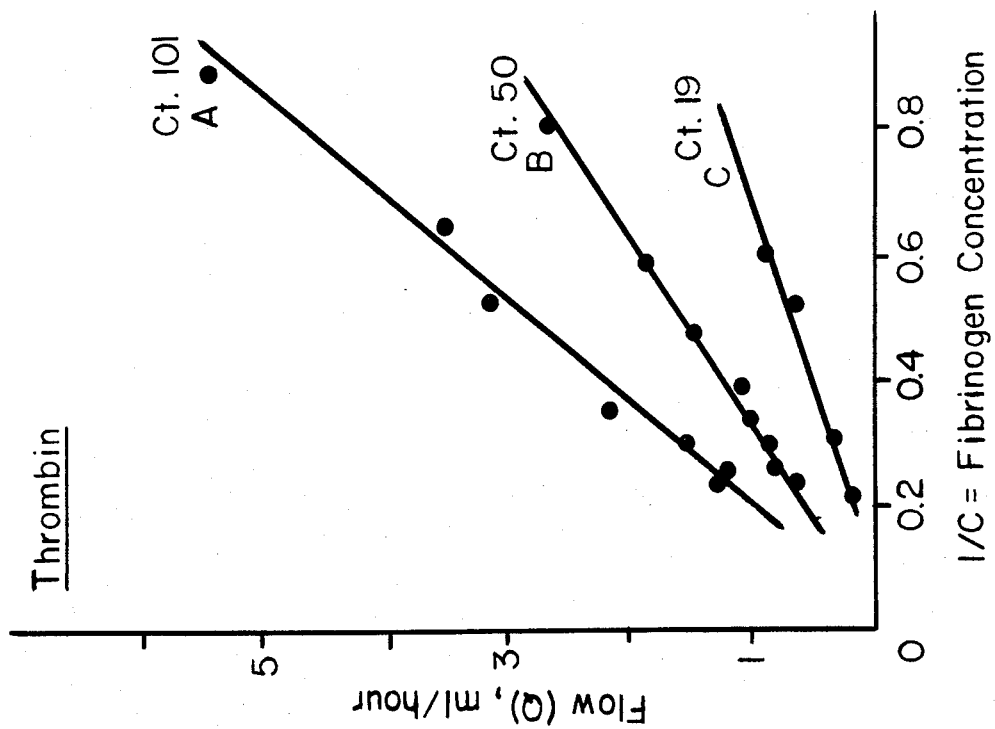

The relationship between protein concentration in the gel forming system and flow-rate was next studied. FIG. 5 shows the result of one series of experiments. It is evident that there exists, at different enzyme concentrations, a linear relationship between flow-rate and inverse protein concentration. The curves for thrombin and Batroxobin gels converge to a more or less common intercept near the origin with increasing protein concentration. The r-values for 15 different 1/C versus flow-rate curves (4–8 experimental points in each) were calculated. Mean r-values and SD were as follows: for thrombin, $0.9738 \pm 0.0308$ and for Batroxobin, $0.9711 \pm 0.0356$.

Figure 2B:
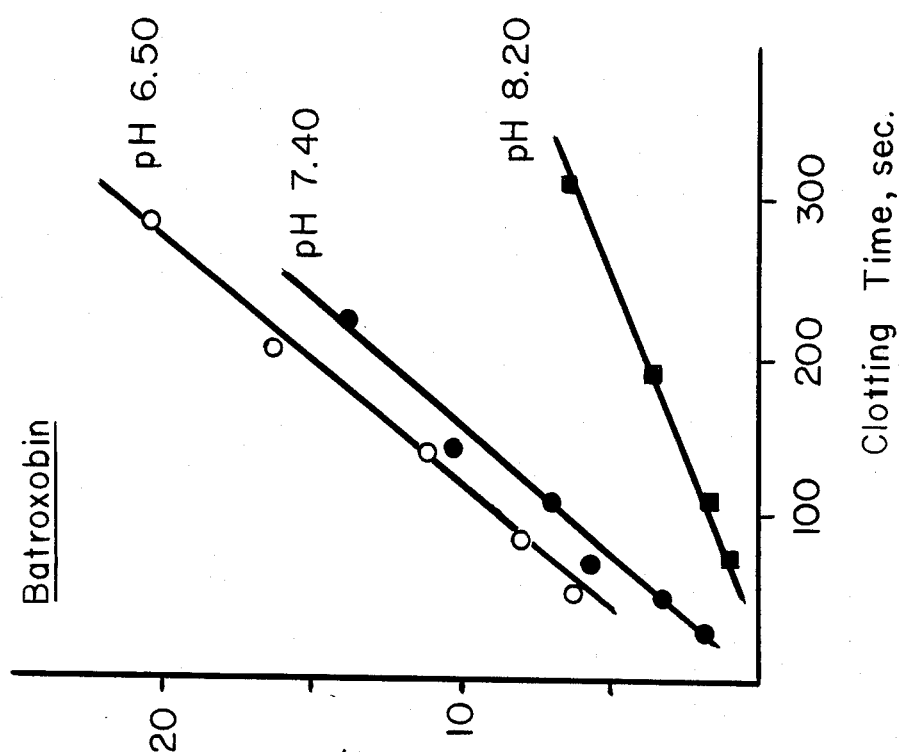
FIGS. 2a and 2b show graphs of the flow as a function of the coagulation time at different pH with thrombin and Batroxobin, respectively.
Figure 2A:
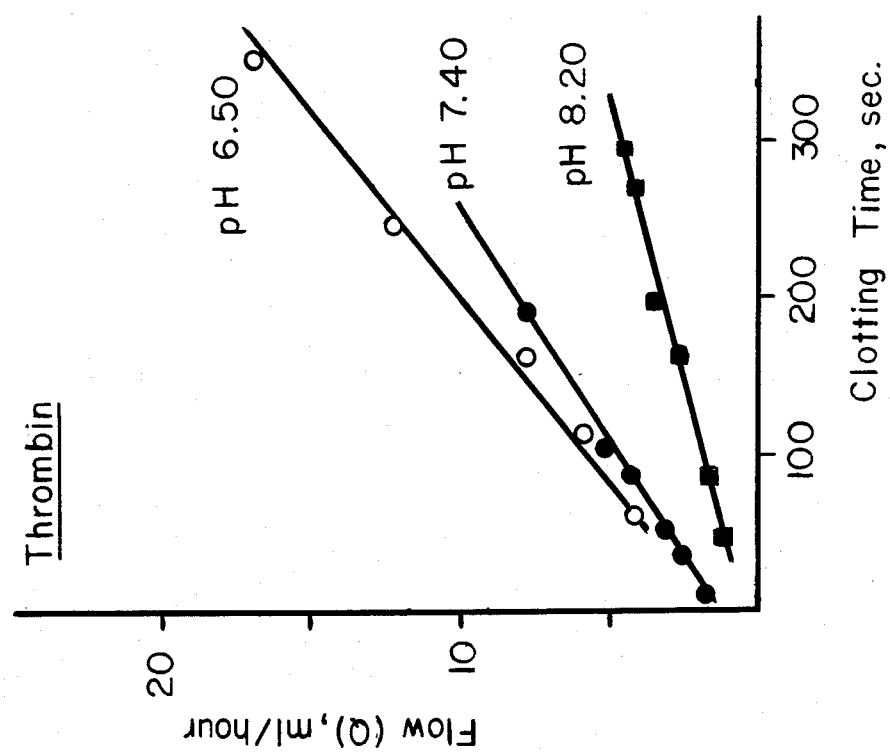
Figure 3:
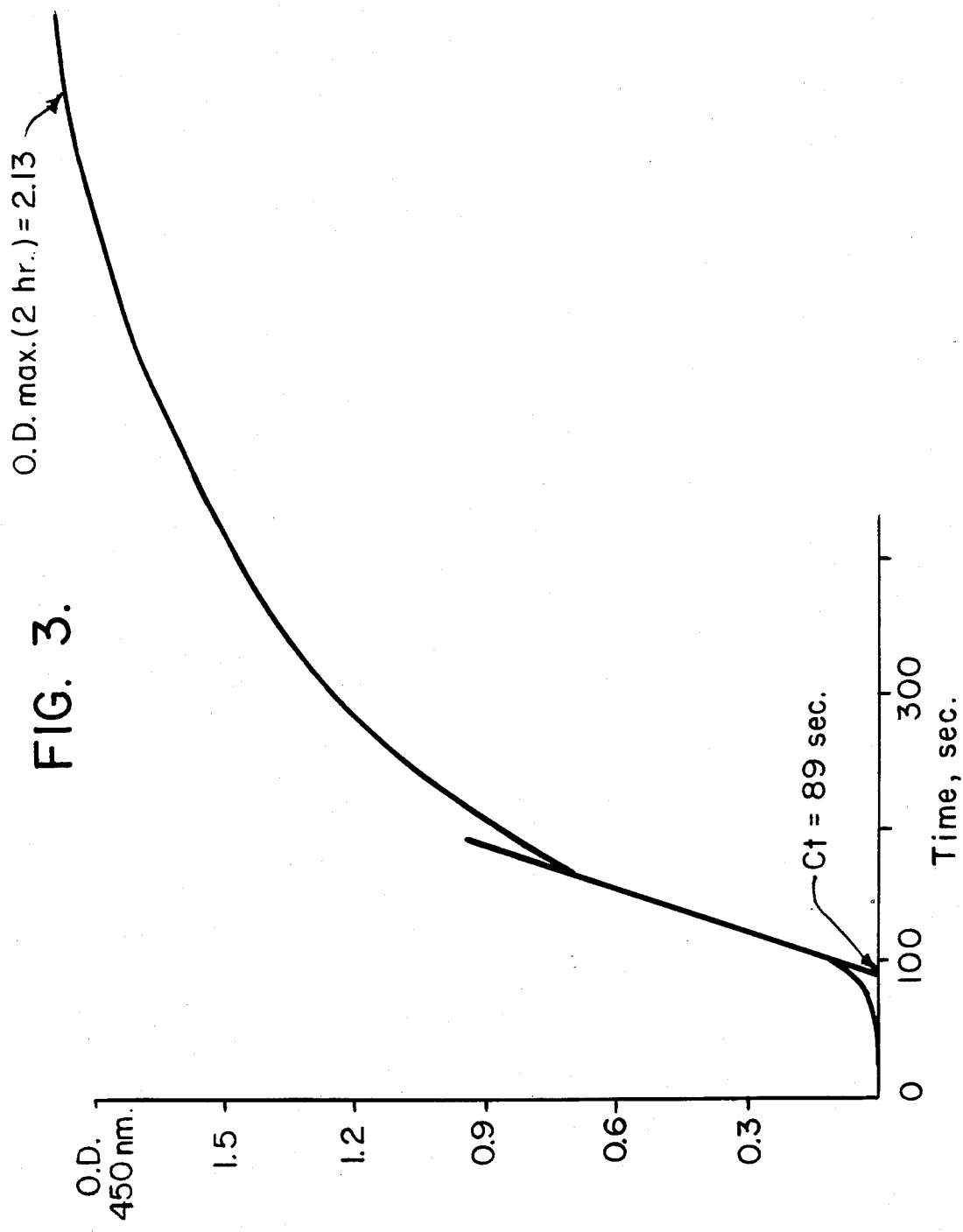
FIG. 3 shows the turbidity of the fibrinogen solution (fibrinogen) as a function of the time after addition of thrombin.

It is apparent from FIG. 2 how the flow rate Q/t, at a constant hydrostatic pressure, is directly proportional to the coagulation time (Ct) of the thrombin-fibrinogen mixture at different pH. The coagulation time of the system is determined spectrofotometrically in a separate test under otherwise identical conditions. The optical density OD at 450 nm is determined. At gel formation the turbidity of the solution increases rapidly as shown in FIG. 3. The tangent of the steepest portion of the curve intersects the time axis at a distance designated as coagulation time Ct. As there is a direct relation between Ct and flow rate Q/t, Ks is also directly correlated with Ct according to equation 1.

It is apparent from FIG. 4 that the flow rate of gels formed at different ionic strength is always directly correlated to the Ct of the enzyme-fibrinogen solution used in the gel preparation. In addition the great influence on the flow rate at a change of the ionic strength is pointed out.

As is apparent from FIG. 5, the flow rate Q/t is inversely proportional to the fibrin concentration (fibrinogen concentration) in the gel. Thus, according to equation 1, Ks will also be inversely proportional to the fibrinogen concentration.

Figure 6B:
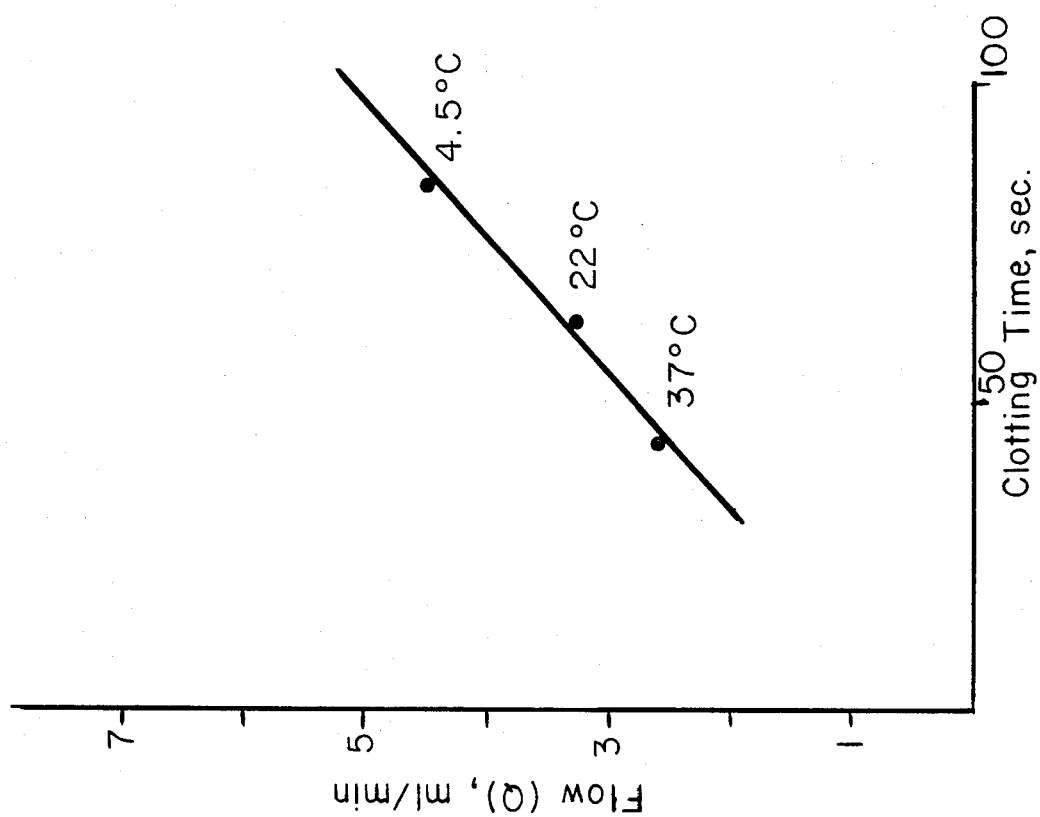
FIGS. 6a and 6b show the temperature plotted against the coagulation time and the flow, respectively, as a function of the coagulation time at different temperatures.
Figure 6A:
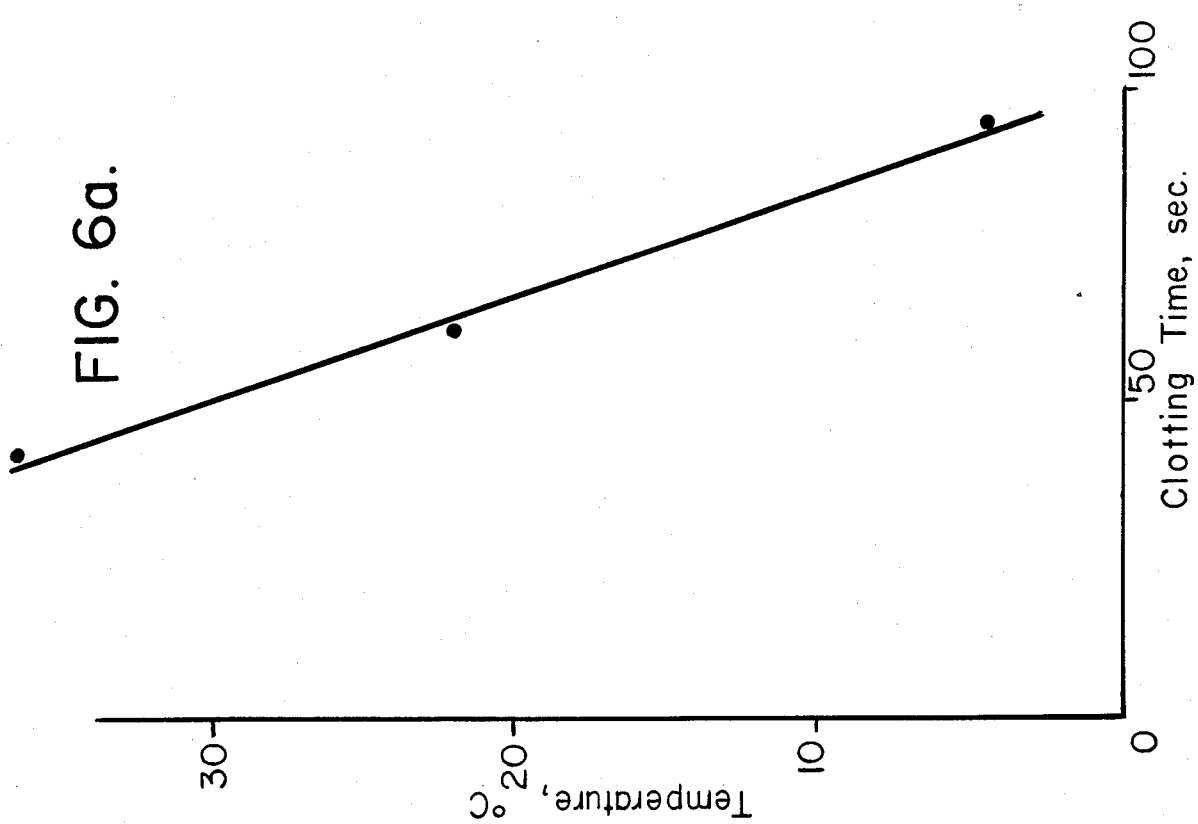

The flow is dependent on the temperature, as according to equation 1, the flow is inversely proportional to the viscosity of the permeation solution. The temperature in gel formation is also of importance as a constant enzyme concentration, Ct is reduced at a higher temperature. This is apparent from FIG. 6a. However, the flow rate in gels formed at different temperatures is directly proportional at Ct at the relative temperature, as is evident from FIG. 6b.

The columns prepared in the way schematically illustrated in FIG. 1 are of small dimensions (1.5 cm$^2 \times$ 2.6 cm). Similar qualitative results are observed with gel columns of greater dimensions (5 cm$^2 \times$ 12 cm). When nothing else is indicated, the smaller type of column is used in the tests.

EXAMPLE 2

Standardization of pore size with latex particles of a known size

Spherical latex particles of diameters between $0.085 \pm 0.0055$ (SD) $\mu$m (SD=standard deviation) and $0.198 \pm 0.0036$ (SD) $\mu$m from Dow Chemicals, USA, were used in the tests. A number of gels formed at pH 7.4 and at two different ionic strengths, were used. In the tests, Ct varied from 23 to 314 seconds. The theoretical radius was calculated for each gel according to equation 3 assuming that a cylindrical vertical capillary system was present.

Figure 7:
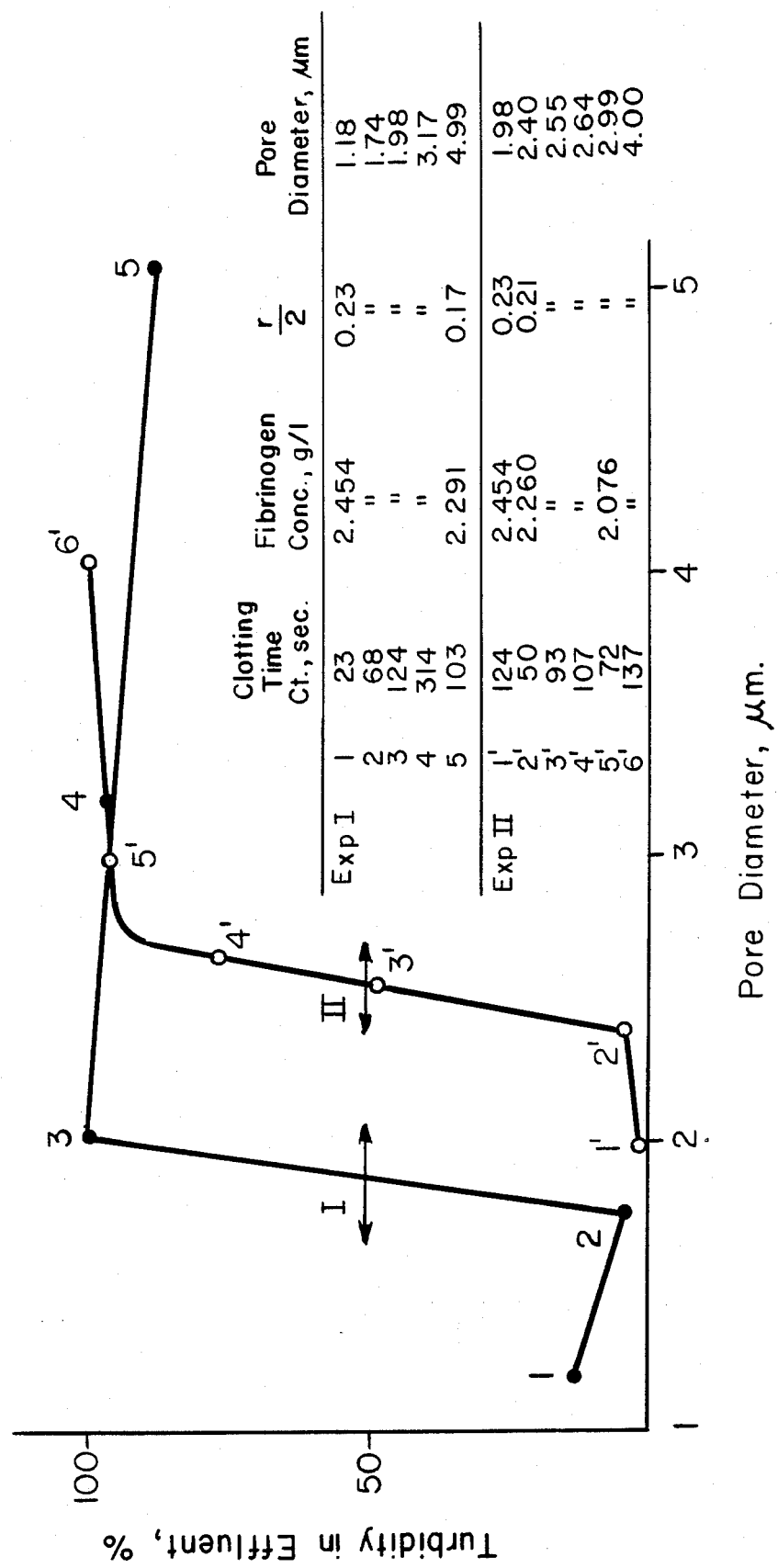
FIG. 7 shows the turbidity of the effluent (turbidity in the effluent) in % as a function of the pore diameter in μm.

FIG. 7 shows two series of tests. In series I the ionic strength was 0.23 during the gel formation and in series II 0.21. The gel columns were equilibrated with water. After this suspensions of particles were applied to the gels. In series I the particle size was 0.085 $\mu$m and in series II 0.198 $\mu$m. The particles were slurried in water to a concentration of 0.1% (weight/volume). The turbidity at (450 nm) of the effluent was determined. It was then possible to establish by means of the turbidity values if the latex particles had passed the filter.

In FIG. 7 the turbidity has been expressed in % of maximum turbidity of the effluent. As is apparent from FIG. 7 the turbidity of the effluent increases above a certain theoretical pore size of the gel. At an additional increase in pore size more particles will pass through the gel (filter) and over a certain pore size a constant amount of particles permeate the gels. The difference in theoretical pore size between no and complete permeation is a measure of the sum of pores and particle variation. The pore size at 50% permeation is an expression of the average size of pores and particles. If the total variation in pore size is within the range of the average particle size $\pm$ 3 SD it can be assumed that the pore size in the gel is uniform.

In FIG. 7 the variation in particle size (average size $\pm$ 3 SD) has been shown with a horizontal line 50% permeation. It is apparent that the total variation can, to a large extent, be explained by the particle variation. It can be concluded from this that the pores in the gels are rather uniform. It is also apparent from FIG. 7 that the theoretical average pore size is about of an order (one ten power) greater than the real effective particle size. Thus, calculation of the pore size according to equation 3 only gives relative values for the pore size.

EXAMPLE 3

Passage of proteins and dextran trough fibrin gels

Various protein solutions were (applied) to fibrin gels prepared in the way described in Example 1. The gel formation was carried out at room temperature (21°–25° C.). In most cases, the buffer used in gel formation had the same composition as the buffer used for permeation. The filtration tests took place at room temperature (22°–25° C.). When nothing else is indicated, the volume of the gels was 1.47 cm$^2 \times$ 2.48 cm=3.65 ml. The tests were carried out on different days and with different fibrinogen preparations. Thus, it is not possible to make a comparison as to the pore size between different tests. Table 1 shows the proteins tested with respect to filtering ability through fibrin gels of different porosities. It is apparent from the table, that proteins, including those having a very high molecular weight, are filtered even through gels having small pore sizes. A high molecular weight polysaccharide ("Blue Dextran") shows the same filtration properties as the proteins. The table shows that the yield of proteins in the eluate is high, from which it appears that at least at room temperature the interaction between gel matrix and proteins is small. This also applied to such proteins as fibrinogen, fibronectin and the factor VIII complex.

TABLE I

Filtration of proteins and particles through fibrin gels

| Test | Diameter or mol. weight | Permeation Buffer | Sample ml | Yield % | Pore diam.(a) μm | Gel formation Ct s | Protein g/l | Γ/2 | pH | Enzyme |
|---|---|---|---|---|---|---|---|---|---|---|
| Human serum | — | TI buffer +Ca$^{2+}$ | 0.1 | 98.2 | 2.12–4.86 (0.125–0.286) | 16–230 | 3.42 | 0.21 | 7.40 | T |
| Human plasma | — | TI buffer −Ca$^{2+}$ | 0.1 | 101.1 | 0.288 | 260 | 4.56 | 0.26 | 7.40 | T |
| Fibrinogen (4 g/l) | 340000 | TI buffer −Ca$^{2+}$ | 1.0 | 93.8 | 4.34 (0.255) | 124 | 2.157 | 0.21 | 7.40 | T |
| Fibrinogen (4 g/l) | 340000 | TI buffer +Ca$^{2+}$ | 1.0 | 97.8 | 2.33 (0.137) | 66 | 2.157 | 0.21 | 7.40 | B |
| Fibronektin (2.3 g/l) | 440000 | TI buffer −Ca$^{2+}$ | 0.4 | 109 | 2.30 (0.135) | 430 | 2.274 | 0.21 | 7.40 | T |
| Antihemophilic factor (FVIII)b | 2–6 × 10$^6$ | TI buffer +Ca$^{2+}$ | 1.0 | 99 8 | 2.48 (0.146) | | 3.000 | 0.21 | 7.40 | T |
| | | | 1.0 | 63 | 1.08 (0.064) | | 5.000 | 0.26 | 7.40 | |
| Ferritin (15 g/l) | 2 × 10$^6$ | TI buffer +Ca$^{2+}$ | 0.2 | 103.8 | 0.276 (0.016) | 440 | 4.56 | 0.26 | 7.40 | T |
| Hemocyanine (11 g/l) | 3 × 10$^6$ | TI buffer +Ca$^{2+}$ | 0.2 | 97.7 | 0.276 (0.016) | 440 | 4.56 | 0.26 | 7.40 | T |
| Washed human red blood corpuscles 5 × 10$^5$/μl | 7 μm | Physiological common salt solution −Ca$^{2+}$ | 0.1 | 0 | 3.60 (0.212) | 255 | 1.66 | 0.21 | 7.40 | T |
| Human Platelets (4 × 10$^5$/μl plasma) | 2–4 μm | TI buffer −Ca$^{2+}$, +10 m M EDTA | 0.3–5 | 0 | 4.86 (0.286) | 228 | 3.42 | 0.21 | 7.40 | T |
| Rat liver mitochondria | 0.5 μm | TI buffer −Ca$^{2+}$ +0.25 M sykros, +10 m M EDTA | 0.3 | 0 | 4.40 (0.259) | 524 | 2.16 | 0.21 | 7.40 | T |
| E. Coli | 0.8 × 1.2μ | TI-buffer −Ca$^{2+}$ | 45 | 0 | 1.78 (0.105) | 24 | 5.00 | 0.21 | 7.40 | T |
| Sendai-virus (640) hamagglutination units/ml | ~0.15 μm | TI buffer −Ca$^{2+}$, + 1% BSA | I 0.2 | 0 | 0.284 (0.017) | 33 | 4.63 | 0.233 | 7.40 | T |
| | | | II 0.2 | 50.3 | 2.36 (0.139) | 19 | 2.08 | 0.21 | 7.40 | T |
| | | | III 0.2 | 95.2 | 4.46 (0.262) | 137 | 2.08 | 0.21 | 7.40 | T |
| Sendaivirus filtered through hardened and autoclaved thin layer fibrin - gel (see Example 6 and Table 2-III) | ~0.15 μm | TI buffer +Ca$^{2+}$ | 5 | — | 0.268 (0.016) | 60 | 9.86 | 0.26 | 7.40 | T |
| in the filtrate | | | | 0.86 | | | | | | |
| on the filter | | | | 85.0 | | | | | | |

(a)The theoretical diameter was calculated according to equation 3. The effective diameter through calibration with latex particles.

The effective pore diameter is given within brackets. (Based on a ratio $\frac{\text{theoretical}}{\text{effective}}$ of about 17)

(b)The volumes of the gel column; 4.9 cm × 11 cm = 53.9 ml.

EXAMPLE 4

Filtration of suspensions of red blood corpuscles through fibrin gels

Fibrin gels were prepared in the way described in Example 1 and the conditions of gel formation is shown in Example 3. A small amount (0.2 ml) of human blood was applied to a gel column. Continued filtration was carried out at room temperature (22°–25° C.) under the conditions shown in Example 3. The blood corpuscles did not pass through the fibrin gel. This was expected as the diameter of the red blood corpuscles (7–8 μm) is much larger than the effective pore diameter of the fibrin gel.

EXAMPLE 5a

Filtration of plasma rich in platelets through fibrin gels

Plasma rich in platelets (PRP) was prepared from blood by centrifugation for 4 minutes at 120 g, the blood being drawn in citrate solution to prevent coagulation. It was centrifugated at 2000 g for 5 minutes to remove the remaining red blood corpuscles and EDTA at a concentration of 10 mM was added to the PRP. 0.5 ml of the PRP was applied to a fibrin gel column prepared in the way described in Example 1. The conditions of gel formation is shown in Example 3 and filtration was continued under the conditions shown in Example 3. To prevent aggregation of the platelets and their adhesion to the gel matrix, EDTA (10 mM) was added not only to PRP but also to the solution which was filtered. No platelets could be demonstrated in the eluate from the fibrin gel column. This was expected as the diameter of the platelet lies between 2 and 4 μm, which is considerably more than the effective pore size of the gel.

EXAMPLE 5b

Separation of mitochondia from fragments of liver cell by filtration through fibrin gels Liver cells of a rat were homogenized in a homogenizator according to Potter-Elvehjem. Separation of cell fragments was achieved by differential centrifugation in known manner. The mitochondria were slurried in a buffer solution containing Na-EDTA (10 mM) and succrose (0.25 M). 0.3 ml of the resulting suspension was applied to a fibrin gel column prepared in the way described in Example 1. The conditions of gel formation is shown in Table I and filtration was continued under the conditions indicated in Table 1. No mitochondria could be demonstrated in the eluate, which was as expected, since their diameter is about 0.5 μm; thus considerably bigger than the effective pore size of the gel.

EXAMPLE 6

Separation of Sendai-virus by filtration through fibrin gels

Sendai virus is a virus specific to mice which is used for preparation of interferon in human lymphocyte cultures. A partially purified virus preparation (640 hemagglutination units/ml) was used in the tests.

0.2 ml of the virus suspension was applied to each of three fibrin gel columns prepared in the way described in Example 1. The conditions of the gel formation appear from Table 1 and filtration was continued under the conditions shown in Table 1. No hemagglutination activity could be demonstrated in the eluate from column I; 50% of hemagglutination activity were demonstrated in the eluate from column II and 95% of the hemagglutination activity of the virus particles was demonstrated in the eluate from column III (see Table 1).

After filtration the silk nets at the upper part of the three columns were washed with a buffer solution (containing 1% of borine serum albumin, BSA) and the hemagglutination activity of the washings was analyzed. In the washing liquid from columns I 100% of the hemagglutination activity was found; in the washing liquid from column II 25% of the activity was found and in the washing liquid from column III no activity was found.

The particle diameter of Sendai virus is stated to be about 0.15 μm. The tests show that when the effective pore radius is more than 0.15 μm the virus particles pass through the gel. When the effective pore radius of the gel is less than 0.15 μm a retention of the particles will, on the other hand, occur.

EXAMPLE 7

Separation of *Eschericia Coli* (*E. coli*) by filtration through fibrin gel

*E. coli* is an elongated intestinal bacterium of the approximate dimensions 0.8×1–2 um. A suspension of *E. coli* in trisimidazole-buffer, free of calcium and with pH 7.4 and ionic strength 0.21, was prepared (see Example 1). The suspension contained between $10^7$ and $10^8$ bacteria/ml. 45 ml of the suspension were supplied to a fibrin gel column of the dimensions 5 cm$^2$×11 cm prepared in the way described in Example 1. The conditions of the gel formation and the filtration are shown in Table 1. The flow rate was 31 ml/h. No bacteria passed through the gel, determined by turbidity measurements of the eluate from the column. The flow rate at constant pressure was less at the end of the test than at its beginning. Assuming an unchanged $K_s$ the reduction of surface corresponding to the reduction in flow can be calculated according to equation 1. According to this calculation the surface had been reduced to 58%. Thus, one might expect that the bacteria were enriched on the upper gel surface. By washing the silk net attached to the upper part of the gel with buffer solution 99% of the bacteria applied to the gel were found in the washing liquid.

The test shows that *E. coli* cannot pass through gels having a pore diameter which is considerably less than the smallest diameter of the bacteria.

EXAMPLE 8

Preparation of gels with reinforcement of porous plastic

In the foregoing examples nets of silk, plastic or metal adapted to the upper and lower portions of the gel have served as stabilizing structure of the fibrin gels. A corresponding stability can also be obtained in such a way that the fibrin gel is cast into a porous plastic, e.g. polyurethane, polyester or some similar porous plastic material, preferably one which is wettable by water.

In this example a foam plastic of polyurethane ("Regilen 40 AG") of a pore size 0.4 mm has been used. The gels were cast in a special apparatus. This consisted of a cylindrical plastic chamber in which the porous plastic had been introduced; the plastic was accommodated in a ring of acrylic plastic (height 2 cm and diameter 9 cm). The apparatus (chamber) had an opening at the upper and lower end, respectively. One opening was connected to a vacuum pump and the other opening was kept closed. The chamber was evacuated by means of the vacuum pump. After this the valve connecting the chamber with the vacuum pump was shut off. A fibrinogen-thrombin solution was subsequently allowed to fill the chamber rapidly through the valve in the opposite opening. The valve was thereafter closed and the chamber was left for 2 hours, so that the fibrinogen solution in the porous plastic material should be completely converted to a fibrin gel. The clotting parameters of the thrombin-fibrinogen mixture was shown in Table 2. For comparison a gel was also prepared in the way described in Example 1. In Table 2 the Ks-value of this latter gel is also shown. After complete gel formation the chamber was opened and the plastic cake with fibrin gel (including its plastic frame) was taken out. It was transferred to a special filter chamber. The framed ring, in which the plastic material and the gel were accomodated, fitted tightly to the edges of the filter chamber through two O-rings. The upper lid of the chamber was provided with an inlet for the liquid to be filtered and a ventilating valve to let our the air above the gel surface. In the lower portion of the chamber there was an outlet for collecting the filtered liquid. A buffer solution with the composition shown in Table 2, was filtered through the gel cake. The Ks value was calculated according to equation 1 (Table 2). As is apparent from the table the Ks-value of the gel, cast in plastic, is of the same order as the gel prepared according to Example 1. The partial specific volume of the plastic material in the gel cake is 0.03 which means that the plastic matrix reduces the surface available for flow only to a small extent.

EXAMPLE 9

Preparation of gels in a cellulose matrix

Cellulose materials can also be used as reinforcing agent (supporting substance). In this example, a porous cellulose compound ("Wehex cloth") is used as reinforcing agent of the fibrin gel. It had a thickness of 0.2–0.3 cm. Circular pieces of a radius of about 3 cm were wetted with a thrombin-fibrinogen solution. The cellulose pieces then swelled to about double thickness. The partial specific volume of the swollen cellulose compound was 0.04. Immediately after swelling which lasted for about 2–4 seconds the pieces were placed on the filter disc of a Büchner funnel. Measures were taken so that the pieces fitted tightly to the edges of the funnel. The openings of the funnel were covered with "Parafilm" and the funnel was left at room temperature for 2 hours in order to obtain a complete fibrin formation in the pores of the cellulose. Buffer solutions, the composition of which is shown in Table 1, were filtered through the gels. The Ks-value of the gels which are cast in cellulose is of the same order of magnitude as control gels prepared without reinforcing substance.

EXAMPLE 10

Preparation of fibrin gels in thin layers for filtration

In this example it is shown that fibrin gels in thin layers with reinforcement only on the lower surface can be used for filtration. About 10 ml of fibrinogen solution in trisimidazole buffer with pH 7.4 were mixed with a thrombin solution. The mixture was thereafter poured into a Petri cup the bottom of which was covered by a damp silk cloth. The cup was covered with a lid and was left for 2 hours for a complete gel formation. The thickness of the gel layer was 2 mm. The clotting parameters of the gel is shown in Table 2. The filter was thereafter attached to a "Millipore" filter support provided with a funnel. The funnel was filled with buffer solution and the flow rate was determined. As is apparent from Table 2 the Ks-value is of the same order or magnitude for a corresponding fibrin gel prepared according to Example 1. However, the filter showed in course of time gradually diminishing Ks-values, which presumably is due to compression of the gel matrix during the flow.

EXAMPLE 11 stabilization of gels by treatment with dialdehyde

In this example it is shown that gels prepared according to Examples 1, 8 and 10 can be stabilized by treatment with dialdehyde.

A. A gel prepared according to Example 1 was first equilibrated with water and then brought into equilibrium with 0.014 M phosphate buffer solution with pH 7.2 in 0.15M NaCl (phosphate buffered saline solution PBA). 2–4 column volumes of a 1% glutaraldehyde solution were then allowed to filter through the gel in the course of 10 minutes–2 hours. After this the gel was washed with several column volumes of PBS and then with water. The column was finally equilibrated with tris-imidazole buffer and flow measurements were carried out. The Ks-value is almost unchanged after treatment with glutardialdehyde. After the flow measurements, the gel was taken out and treated for 72 hours with 8 M urea containing 1% of sodium dodecyl sulphate (SDS). The gel was then reduced with 1% dithiotreitol in a way known per se. Polyacrylamide gel electrophoresis in the presence of SDS showed in comparison with non-stabilized gels the absence of free fibrin chains (fibrinogen chains), which can be interpreted as a proof that glutardialdehyde had cross-linked the chain units of the fibrin structure.

B. A gel prepared in porous plastic according to Example 8 was first washed with a tris-imidazole buffer solution free of calcium and was then brough into equilibrium with a 0.014M phosphate buffer solution with pH 7.2 in 0.15M NaCl (PBS). Two column volumes of a 1% glutar dialdehyde solution were then passed through the gel cake (column) in the course of 10 minutes. The gel cake was then washed with several column volumes of PBS and then with water. Finally the column was brought into equilibrium with tris-imidazole buffer and flow measurements were carried out. These are shown in Table 2. As is apparent from the Table the Ks-value is only slightly changed after the treatment with glutardialdehyde and is of the same order of magnitude as a gel prepared according to Example 1. The gel stabilized with glutardialdehyde was then autoclaved at 120° C. for 20 minutes at a pressure of 1.4 atm. After autoclaving the flow of buffer solution was again tested through the gel cake. As is apparent from Table 2, autoclaving has influenced the flow properties of the gel only to a small extent. Cracks in the gel would have caused drastic increase, of the flow through the gel.

C. A fibrin gel prepared according to Example 10 was transferred to a cup with 500 ml water to remove buffer salts by diffusion. After 2 hours the gel was transferred to a cup with a new portion of water. After 2 hours the gel was transferred to a cup with 500 ml phosphate buffer solution with pH 7.2 in 0.15M NaCl (PBS) and was left over night. The gel was then transferred to a Petri cup containing 50 ml of 1% glutar dialdehyde. After 2 hours the glutardialdehyde solution was exchanged for a new portion of the same liquid. After additional 2 hours the gel was transferred to a cup with water and washed in the way described above. After washing with water the gel was transferred to a cup with tris-imidazole buffer solution. After 2 hours the washing liquid was exchanged for a new portion and after additional 12 hours the gel was transferred to a "Millipore"-filter carrier with a funnel. As a comparison measurements were carried out with a gel prepared in the same way except the treatment with glutar dialdehyde. Directly after casting, this gel was transferred to a "Millipore" filter container for flow measurements. As is apparent from Table 2 the flow through the vulcanized filter was comparable with that through the non-vulcanized filter at the start of the flow measurement. However, at the end of the measuring period, the $K_s$-value of the nonstabilized filter had been reduced to a large extent which was not the case with the vulcanized filter. After the flow measurement the filters were sterilized through autoclaving of the filter (and the filter apparatus) at 120° C. for 20 minutes at the pressure 1.4 atm. Flow measurements were carried out after the heat treatment and the $K_s$-values are shown in Table 2.

No flow could be demonstrated through the nonstabilized filter. On the other hand the vulcanized filter showed $K_s$-values of the same order before as well as after autoclaving.

5 ml of a suspension of Sendai-virus were supplied to the vulcanized filter. Filtration was carried out by means of a water suction. When the liquid had passed the filter additional 5 ml of buffer solution were passed through the filter. This was repeated twice. The filtrate was tested for hemagglutination activity. Inconsiderable hemagglutination activity could be demonstrated. The upper surface of the filter was washed with several portions of buffer solution. The washing liquid was opalescent and its hemagglutination activity corresponded to a yield of virus particles of almost 100%.

These examples show that the filters can be stabilized with a dialdehyde such as glutardialdehyde.

TABLE 2

| Type of filter | | Buffer | Permeation Pressure dyn/cm$^2$ | $K_s$ cm$^2$ | Diameter μm | Gel formation Ct, s | fbg. konk. g/l | m 2 | pH | temp, °C. |
|---|---|---|---|---|---|---|---|---|---|---|
| I | a Fibrin gel in foam plastic | TI +Ca$^{2+}$ | — | 5.82 × 10$^{-9}$ | 4.38 (0.258) | 171 | 2.478 | 0.21 | 7.4 | 23 |
| | b Vulcanization | TI +Ca$^{2+}$ | — | 5.20 × 10$^{-9}$ | 4.14 (0.243) | " | " | " | " | " |
| | c Vulcanization and sterilization | TI +Ca$^{2+}$ | — | 1.39 × 10$^{-9}$ | 2.14 (0.126) | " | " | " | " | " |
| | d Control | TI +Ca$^{2+}$ | — | 3.15 × 10$^{-9}$ | 3.17 (0.264) | " | " | " | " | " |
| II | Fibrin gel in cellulose sponge | TI, +Ca$^{2+}$ | 3430 | 0.61.0 × 10$^{-11}$ | 0.139–0.0180 (0.008–0.011) | 60 | 9.864 | 0.26 | .7.4 | 24 |
| | Control | TI, +Ca$^{2+}$ | 29400 | 1.14 × 10$^{-11}$ | 0.192 (0.011) | " | " | " | " | " |
| III | a Thin layer fibrin gel | TI +Ca$^{2+}$ | 7350 | 1.0–2.5 × 10$^{-11}$ | 0.180–0.284 (0.011–0.017) | 60 | 9.864 | 0.26 | 7.4 | 24 |
| | b Vulcanization | TI +Ca$^{2+}$ | 7350 | 3.6 × 10$^{-11}$ | 0.343 (0.020) | " | " | " | " | " |
| | c Vulcanization and sterilization | TI +Ca$^{2+}$ | 7350 | 2.24 × 10$^{-11}$ | 0.269 (0.016) | " | " | " | " | " |
| | d Vulcanization and sterilization | TI +Ca$^{2+}$ | 9.86 × 10$^5$ | 3.52 × 10$^{-12}$ | 0.107 (0.0063) | " | " | " | " | " |
| | e. Vulcanization and sterilization | TI +Ca$^{2+}$ | 7350 | 1.66 × 10$^{-11}$ | 0.232 (0.014) | " | " | " | " | " |
| | f Control | TI +Ca$^{2+}$ | 29400 | 1.14 × 10$^{-11}$ | 0.192 | 60 | 9.864 | 0.26 | 7.40 | 24 |

TI = tris-imidazol buffer
See also explanation to Table I

What is claimed is:

1. A filter comprising fibrin in gel form, said gel having substantially uniform pore sizes, said filter comprising means for retaining the shape of at least the upper surface of said gel against deformation when contacted by a flowing medium, said means for retaining the shape comprising a foraminous sheet member or a foam.

2. A filter according to claim 1 wherein said shape-retaining means comprises a foraminous sheet member.

3. A filter according to claim 2 wherein said foraminous sheet member is in contact with said gel.

4. A filter according to claim 3 wherein said foraminous sheet member comprises a fibrous network.

5. A filter according to claim 4 wherein said network comprises a woven fabric.

6. A filter according to claim 4 wherein said network comprises a knitted fabric.

7. A filter according to claim 4 wherein said network comprises a non-woven fabric.

8. A filter according to claim 4 wherein said fibrous network comprises a sheet containing silk.

9. A filter according to claim 4 wherein said fibrous network comprises a sheet containing nylon.

10. A filter according to claim 4 wherein said fibrous network comprises a sheet containing cellulose.

11. A filter according to claim 4 wherein said fibrous network comprises a sheet containing cotton.

12. A filter according to claim 4 wherein said fibrous network comprises a sheet containing a natural fiber.

13. A filter according to claim 4 wherein said fibrous network comprises a sheet containing a synthetic fiber.

14. A filter according to claim 2 wherein said shape-retaining means comprises a plurality of wires which intersect one another.

15. A filter according to claim 14 wherein said wires are in contact with said gel.

16. A filter according to claim 15 wherein said wires are in the form of a wire screen.

17. A filter according to claim 15 wherein said wires are in the form of a wire mesh.

18. A filter according to claim 15 wherein said wires are in the form of an expanded wire sheet.

19. A filter according to claim 15 wherein said wires are metal wires.

20. A filter according to claim 1 wherein the average effective size of said fibrin gel is 0.003 to 1.0 μm.

21. A filter according to claim 1 wherein the average effective size of said firbin gel is 0.009 to 0.3 μm.

22. A filter according to claim 1 wherein said fibrin gel is formed by contacting fibrinogen with an enzyme.

23. A filter according to claim 22 wherein said enzyme is a coagulation enzyme.

24. A filter according to claim 23 wherein said coagulation enzyme is selected from the group consisting of thrombin, Batroxobin, Arvin, Eccarin, Papain, Staphylocoagulase, Trypsin, caterpillar venom enzyme.

25. A filter according to claim 23 wherein said fibrinogen is brought in contact with said enzyme in the presence of at least one calcium ion.

26. A filter according to claim 25 wherein the calcium ion concentration in the gel formation mixture is up to 20 mM.

27. A filter according to claim 23 wherein the enzyme is thrombin and the gel is prepared in the absence of a calcium ion.

28. A filter according to claim 25 wherein said enzyme is Batroxobin.

29. A filter according to claim 1 wherein said fibrin gel is a crosslinked fibrin gel and said shape-retaining means is a crosslinking agent.

30. A filter according to claim 29 wherein said crosslinking agent is selected from the group consisting of dialdehydes, azides, aromaticdihalides, and bis-imidates.

31. A filter according to claim 29 wherein said crosslinking agent is glutardialdehyde.

32. A filter according to claim 1 wherein said gel is crosslinked and said shape-retaining means comprises a foraminous sheet member.

33. A filter according to claim 32 wherein said foraminous sheet member comprises a fibrous network.

34. A filter according to claim 1 wherein said gel has disposed on its lower surface a second shape-retaining means.

35. A filter according to claim 34 wherein said second shape-retaining means comprises a forminous sheet.

36. A filter according to claim 1 wherein said gel is adhesively secured to said shape-retaining means.

37. A filter according to claim 1 wherein said gel is grafted to said shape-retaining means.

38. A filter according to claim 1 wherein said shape-retaining means is a foraminous member having pores or openings of a size of 0.01 to 5 mm.

39. A filter according to claim 1, wherein said shape-retaining means comprises a foam.

40. A filter according to claim 39, wherein said foam is a plastic foam.

41. A filter according to claim 40, wherein said plastic is polyurethane.

* * * * *